United States Patent [19]
Muller

[11] Patent Number: 5,885,275
[45] Date of Patent: Mar. 23, 1999

[54] MEDICAL SPACING GUIDE

[75] Inventor: David F. Muller, Boston, Mass.

[73] Assignee: Diomed, Inc., Boston, Mass.

[21] Appl. No.: 7,845

[22] Filed: Jan. 15, 1998

[51] Int. Cl.⁶ .................................................. A61B 17/36
[52] U.S. Cl. ............................................................ 606/17
[58] Field of Search ............................... 606/2, 3, 10, 11,
606/12, 13, 14, 15, 16, 17, 19, 4, 5, 6

[56] References Cited

U.S. PATENT DOCUMENTS

| | | | |
|---|---|---|---|
| 3,865,113 | 2/1975 | Sharon et al. | 606/19 |
| 4,185,633 | 1/1980 | Prozorov et al. | 606/9 |
| 4,978,186 | 12/1990 | Mori | 606/9 |
| 5,125,922 | 6/1992 | Dwyer et al. | 606/3 |
| 5,129,896 | 7/1992 | Hasson | 606/15 |
| 5,163,935 | 11/1992 | Black et al. | 606/17 |
| 5,217,455 | 6/1993 | Tan | 606/9 |
| 5,300,097 | 4/1994 | Lerner et al. | 607/93 |
| 5,342,358 | 8/1994 | Daikuzono | 606/45 |
| 5,344,418 | 9/1994 | Ghaffari | 606/9 |
| 5,360,424 | 11/1994 | Klopotek | 606/4 |
| 5,454,807 | 10/1995 | Lennox et al. | 606/15 |
| 5,468,238 | 11/1995 | Mersch | 606/15 |
| 5,527,350 | 6/1996 | Grove et al. | 607/89 |
| 5,582,608 | 12/1996 | Brown | 606/4 |
| 5,630,811 | 5/1997 | Miller | 606/9 |

*Primary Examiner*—Michael Peffley
*Assistant Examiner*—Sonya Harris-Ogugua
*Attorney, Agent, or Firm*—Nutter, McClennan & Fish, LLP

[57] ABSTRACT

A system is provided to position an energy delivery handpiece a desired distance from a treatment site while at the same time protecting the handpiece, and energy transmitting optical fibers, from soiling due to tissue debris. The system includes one or more energy transmissive members that are formed from a material that allows the passage of electromagnetic (e.g., laser) energy therethrough. The energy transmissive members can be removably and replaceably attachable to one end of a spacer member. An opposite end of the spacer member is mountable to the energy delivery handpiece. The energy transmissive member is effective protect the handpiece from tissue eruptions. In one embodiment the energy transmissive member also is effective to focus electromagnetic energy upon the treatment site.

3 Claims, 3 Drawing Sheets

MEDICAL SPACING GUIDE

CROSS-REFERENCE TO RELATED APPLICATIONS

Not applicable.

STATEMENTS REGARDING FEDERALLY SPONSORED RESEARCH

Not applicable.

FIELD OF THE INVENTION

The present invention relates to energy treatment systems and more particularly to a system for positioning and protecting an electromagnetic energy delivery handpiece adapted for treating a selected area of tissue.

BACKGROUND OF THE INVENTION

Lasers and other such devices are used in various surgical procedures for therapeutically treating tissue, such as skin tissue. For example, medical lasers are used to treat naturally occurring skin lesions and discolorations including freckles, age spots, birth marks, melanomas, nevi, and lentigines. Lasers are also used to remove other visible skin features such as tattoos and "port wine" stain birth marks which are caused by a plurality of enlarged blood vessels. A patient may choose to have such skin features treated for cosmetic reasons and/or medical necessity.

Generally a medical laser for use in treating skin tissue has a handpiece adapted for manipulation by an operator. The handpiece is coupled to a source of laser energy by a cable that can have an optical fiber for carrying the laser energy to the handpiece. The handpiece is guided to a predetermined distance from the treatment area, i.e., skin surface, by a distance gauge or standoff. For example, U.S. Pat. No. 5,217,455 discloses a method for treating skin tissue with laser energy emitted from a medical laser handpiece having a distance gauge that is placed against the skin to focus the laser energy to a chosen treatment area. The distance gauge is a rod-like member extending from a distal end of the handpiece. U.S. Pat. No. 5,454,807 discloses a catheter-type laser energy delivery system for treating tissue. The catheter used with such a system includes a distal tip assembly having a body with an optical fiber disposed therein. An adjustable standoff extends from alongside the body to maintain a proper distance from the end of the optical fiber and the surface of the tissue to be treated. The above-cited references are incorporated by reference herein.

To treat a portion of skin, a suitably trained operator positions the handpiece in a desired location with the standoff placed in contact with the skin of a patient. The standoff maintains a predetermined distance between the handpiece and the skin surface. The operator activates the handpiece to energize a desired tissue area. As the laser energy contacts skin tissue, debris in the form of energized skin tissue is projected away from the treatment site. This tissue debris can be propelled to the energy-emitting end of the optical fiber thereby distorting and/or blocking the flow of laser energy to the treatment area.

It would be desirable to provide a system for focusing energy to a desired treatment site, while also protecting a energy delivery handpiece from tissue debris emanating from the treatment site.

SUMMARY OF THE INVENTION

The present invention provides a system for positioning and focusing an electromagnetic energy delivery system, such as a laser energy delivery system, at a selected treatment site. In one embodiment, the system includes an energy transmissive member positioned at a predetermined distance from a distal end of the laser handpiece. The energy transmissive member protects the laser handpiece from tissue eruptions as laser energy is applied to the treatment site. In one embodiment, the energy transmissive member also focuses laser energy upon the treatment site. Although the invention is primarily shown and described in conjunction with a laser system and handpiece for treating skin tissue, it is understood that the invention is applicable in a variety of additional electromagnetic energy delivering surgical instruments and procedures.

The system includes an energy transmissive member adapted for placement on or near a selected area of tissue to focus laser energy to a treatment site. In one embodiment, the energy transmissive member is removably and replaceably secured to a spacer member which itself is mountable upon a laser handpiece. This coupling arrangement enables the energy transmissive member to be secured in a predetermined position with respect to the laser handpiece. The advantages of the system include the ability of the energy transmissive member to protect the handpiece from soiling by any tissue eruptions that may occur at the treatment site. Further, the energy transmissive member can be used to focus the laser energy from the handpiece to the treatment site as well.

To effect treatment of a selected tissue area, the handpiece is manipulated by an operator to position the handpiece relative to the treatment site. The energy transmissive member is placed in proximity to the treatment site and the handpiece is actuated by the operator to emit laser energy. Laser energy is then focussed, optionally with the aid of the transmissive member, to a desired location at or below a surface of the tissue. The presence of the transmissive member in proximity to the treatment site and spaced apart from the handpiece prevents any tissue debris from contacting the handpiece and blocking or distorting the laser energy emitted from the handpiece.

In another embodiment of the invention, a laser positioning system includes a supply of energy transmissive members, each having different thicknesses and shapes. The energy transmissive members can be secured directly to the laser handpiece, or mounted on a spacer member that is affixed to the laser handpiece. A surgeon can select a suitable energy transmissive member that is most effective to focus laser energy at a treatment site at or below a tissue surface of the tissue.

BRIEF DESCRIPTION OF THE DRAWINGS

The invention may be more fully understood from the following description of the drawings in which.

DETAILED DESCRIPTION OF THE INVENTION

Figure 1:
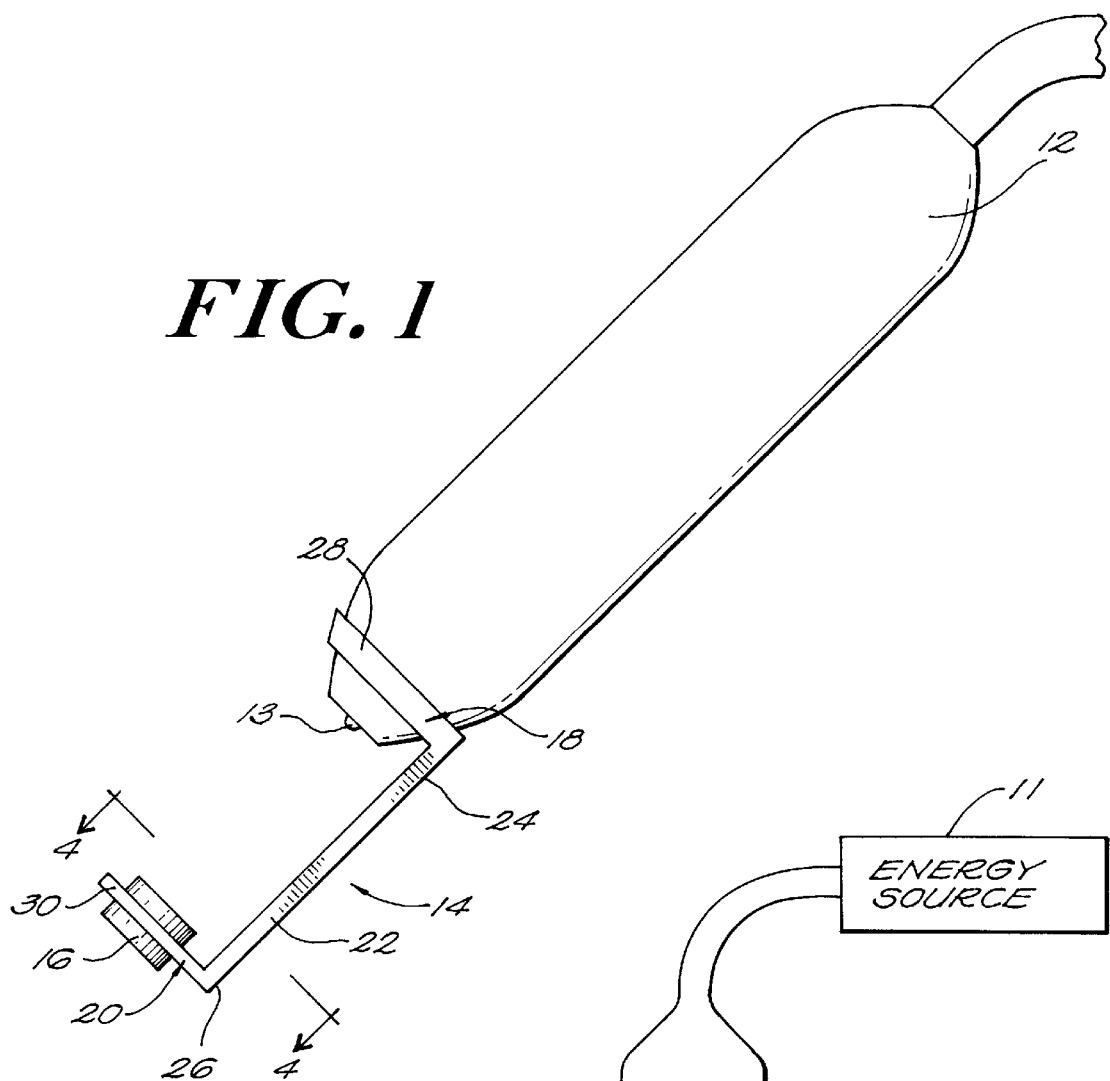
FIG. 1 is a schematic view of the laser positioning system according to the present invention.
Figure 2:
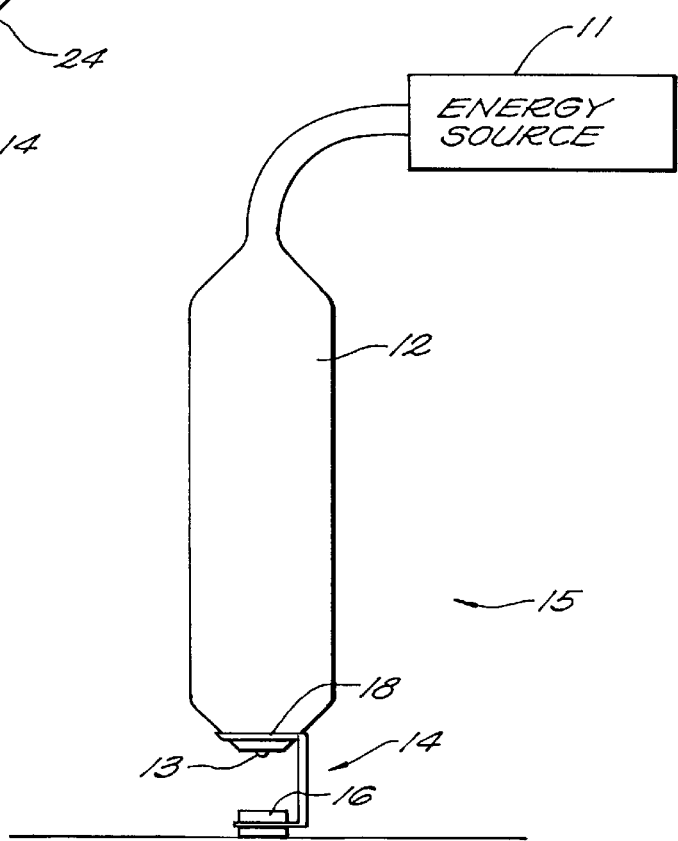
FIG. 2 is a perspective view of a portion of the laser positioning system shown in FIG. 1.

FIGS. 1–2 illustrate an exemplary electromagnetic energy delivery positioning system, such as a laser positioning system 10, in accordance with the present invention. The system 10 includes an electromagnetic energy source 11, such as a source of laser energy. An optical fiber system 15 conveys the energy from source 11 to a handpiece 12 which can be manipulated by a surgeon. A distal end 13 of optical fiber may extend from a distal end 19 of handpiece 12.

The system further includes a spacer member 14 having a proximal end 18 that is mountable upon the handpiece 12 and a distal end 20. The distal end 20 of spacer member 14 is constructed, as described below, so as to be able to selectively engage an energy transmissive member 16 that is removably and replaceably mounted thereon. With the aid of the spacer member 14, the energy transmissive member 16 can be positioned on or near a treatment site and separated from the handpiece 12 by a predetermined distance. The energy transmissive member 16 is effective to protect the distal end of the handpiece 12, including the optical fiber 13 and any lens (not shown) coupled therewith, from tissue debris that may erupt from the treatment site 25 as laser energy contacts the tissue. Optionally, the energy transmissive member 16 can also be used to focus laser energy at the treatment site 15.

The laser positioning system 10 is useful in conjunction with a variety of medical lasers for treating selected areas of skin tissue to treat a variety of dermatological conditions, including the removal of freckles, age spots, birth marks, lesions, tattoos, hair and varicose veins. The type of laser energy to be applied to the target tissue is selected based on the properties of a particular type of laser energy in conjunction with the characteristics of the tissue to be treated. Exemplary useful lasers include diode, Alexandrite, ruby, pulsed dye, and gas ion lasers.

The applied laser energy is defined by various characteristics including wavelength, pulse duration, fluence, spot size, and peak and average power. The laser energy characteristics are selected in accordance with the intended application and the particular needs of a given patient. The wavelength of the laser energy can range up to about 810 nanometers and is typically applied in pulses as known to one of ordinary skill in the art.

The spacer member 14 can have a variety of configurations that securely position the energy transmissive member 16 at a desired distance from the laser handpiece 12. The spacer member 14 should be of sufficient rigidity to resist pressure applied to the handpiece 12 by an operator, and it should not significantly obstruct the operator's view. In one embodiment, the spacer member 14 includes a proximal end 18 that mounts upon the handpiece 12 and a distal end 20 for receiving and holding an energy transmissive member 16. One or more elongate members 22 can extend between the proximal and distal ends 18,20 of the spacer member 14.

The elongate member 22 can vary in length to achieve a desired distance between the distal end of the optical fiber 13 and the energy transmissive member 16. One of ordinary skill in the art can readily determine a suitable length for the elongate member 22. In an exemplary embodiment, the length of the elongate member can range from about 5 to 15 mm.

The elongate member 22 can be of a predetermined length, or it can have an adjustable length. Where the elongate member 22 does not have an adjustable length, a plurality of elongate members 22, each with different lengths, may be provided as part of a system. An elongate member of a desired length can be selected as appropriate for a given procedure.

Figure 6A:
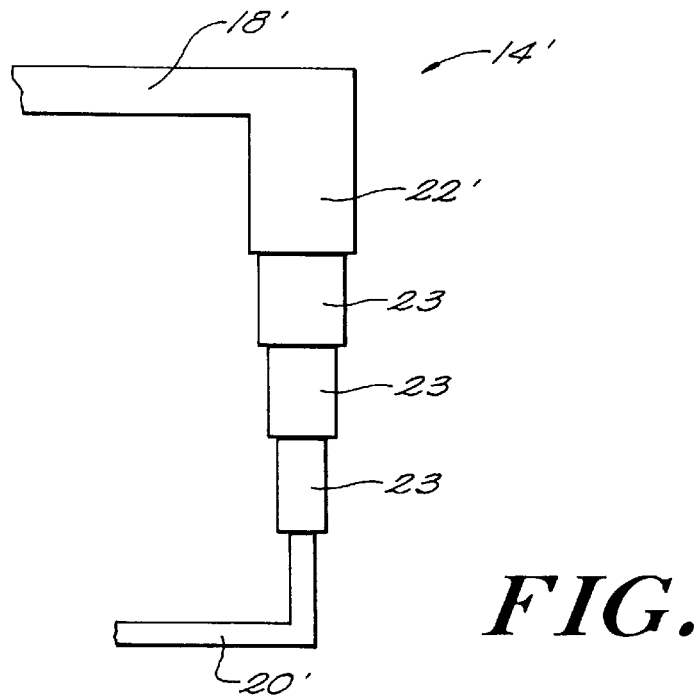
FIG. 6A is a front view of an exemplary embodiment of a spacer member forming a portion of a laser positioning system according to the present invention.
Figure 6B:
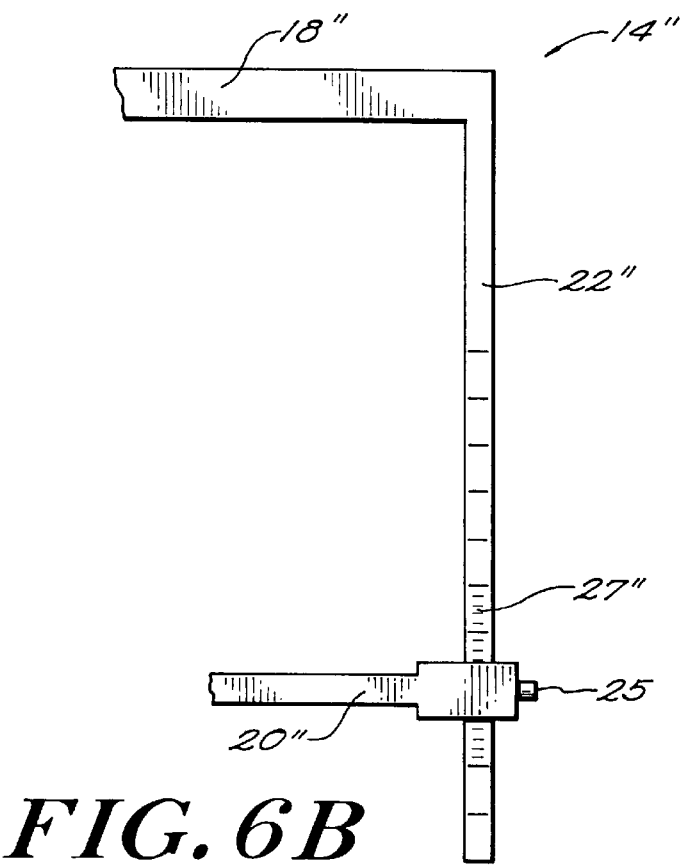
FIG. 6B is a front view of an alternate embodiment of the spacer member of FIG. 6A.

FIGS. 6A and 6B show exemplary adjustable length spacer members. In FIG. 6A, the elongate member 22' of the spacer member 14' includes a series of sections 23 arranged in a telescoping configuration. The distal end 20' of the spacer member 14' can be extended and retracted with respect to the proximal end 18' to provide a selected length for the elongate member 22'. In FIG. 6B, the distal end 20" of the spacer member 14" is slidable along the elongate member 22". The distal end 20" is secured in position by means of a set screw 25 that impinges upon the elongate member 22". The elongate member 22" can also include a series of spaced markings 27 that indicate the position of the distal end 20" with respect to the elongate member.

The proximal end 18 of the spacer member 14 can be adapted for permanent or removable engagement to the handpiece. Removable engagement mechanisms include a ring, mountable upon the handpiece and having a threaded inner portion for engagement with complementary threads on the handpiece. Other removable engagement mechanisms may also be used to attach proximal end 18 to hand piece 12, including detent mechanisms and other positive and/or negative surface features. The proximal end 18 may be permanently attached to the handpiece by a variety of techniques including adhesive bonding and welding.

Figure 3:
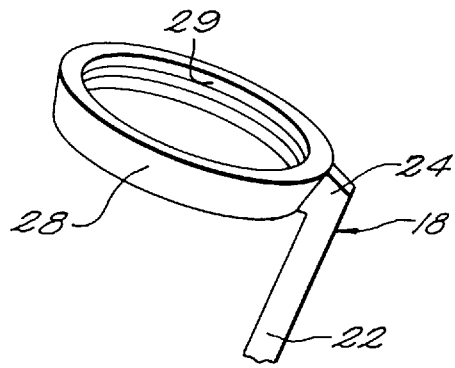
FIG. 3 is a perspective view of a portion of the laser positioning system of FIG. 1.

In one embodiment shown in FIG. 3, the proximal end 18 of the spacer member 14 includes a ring 28 coupled to a first end 24 of the elongate member 22. The ring 28 includes a threaded inner surface 29 for removable engagement with complementary threads (not shown) disposed on the handpiece 12.

The distal end 20 of the spacer member 14 is secured to or is integral with a second end 26 of the elongate member 22. The distal end 20 is adapted to receive and secure at least one energy transmissive member 16. The distal end 20 of the spacer member 14 can be formed in a variety of configurations such that the energy transmissive member 16 remains in a fixed position and resists displacement in the presence of downward pressure applied to the handpiece 12 by the operator. The distal end 20 can be adapted for permanent or removable insertion of an energy transmissive member.

The distal end 20 of the spacer member 14 can include one or more positive and/or negative surface features for engaging complementary surface features of the energy transmissive member 16. Such surface features can provide an interference or snap-fit engagement between the transmissive member 16 and the distal end 20. Alternatively, threads can be formed on an outer surface of an energy transmissive member 16 to engage complementary threads on the distal end 20 of the spacer member 14.

Figure 4:
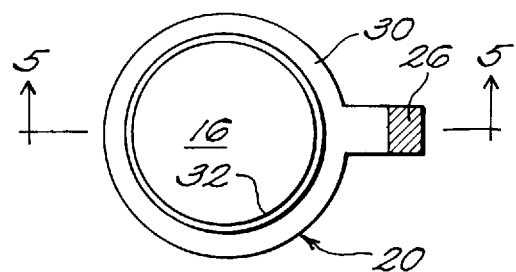
FIG. 4 is a top view, in partial cross-section along lines 4—4, of a portion of the laser positioning system of FIG. 2.
Figure 5:
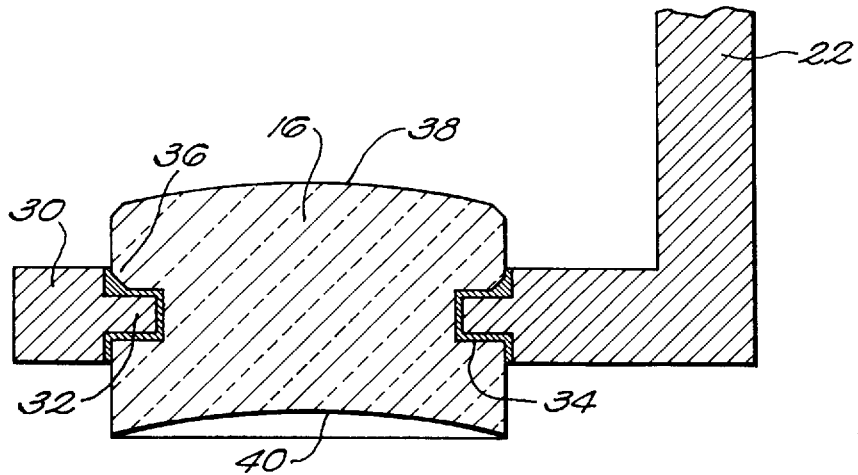
FIG. 5 is a cross-sectional view of the laser positioning system of FIG. 4 along lines 5—5.

FIGS. 4–5 show exemplary embodiments of the distal end 20 of the spacer member 14 having an energy transmissive member 16 secured thereto. The distal end 20 of the spacer member 14 includes an annular member 30 extending from the second end 26 of the elongate member 22. The annular member 30 has an inner surface with a boss 32 disposed thereon. The boss 32 is adapted for engagement within a negative surface feature 34, in the form of a groove, that is formed about the circumference of the energy transmissive member 16. The groove 34 can have a beveled portion 36 to facilitate the insertion of the energy transmissive member 16 within the annular member 30.

It is understood other embodiments to secure the energy transmissive member to the spacer member will be readily apparent to one of ordinary skill in the art.

One of ordinary skill in the art will readily appreciate that the overall shape and dimensions of the energy transmissive member 16 can vary. The energy transmissive member 16 can be cylindrical, square, triangular, and multi-sided. Similarly, the thickness of the energy transmissive member can be relatively constant or can vary in a manner similar to that of an optical lens. That is, the energy transmissive member 16 can be bi-convex, plano-convex, convexo-concave, bi-concave, plano-concave, and concavo-convex.

In one embodiment, the energy transmissive member 16 is cylindrical, i.e., lens-shaped, with a slightly convex entry surface 38 and a slightly concave exit surface 40. The entry surface 38 is curved to reduce the amount of energy that is reflected directly back to the distal end of the optical fiber 13 (FIG. 1). The exit surface 40 is sufficiently concave to focus the laser energy to a predetermined distance from the energy transmissive member 16. It is understood, however, that the energy transmissive member 16 can be shaped such that the laser energy does not converge, or such that it diverges slightly.

As noted above, the dimensions of the energy transmission member will vary depending upon the requirements of a given application. One of ordinary skill in the art will readily appreciate suitable dimensions. In an exemplary embodiment, however, the thickness of the energy transmissive member 16 can vary from about one millimeter to about ten millimeters. Further, the cross-sectional area of the entry surface 38 can range from about 0.01 square centimeter to about 5.00 square centimeters. It is understood that a laser positioning system may include a selection of energy transmissive members, each with different shapes, dimensions and optical properties.

Once a selected treatment area is identified, an operator selects a particular energy transmissive member 16 having appropriate thickness and, optionally, focusing properties. The operator then determines a desired distance between the optical fiber 13 and the energy transmissive member 16 and selects a spacer member 14 with a suitable length or adjusts the elongate member 22 to a desired length. The appropriate energy transmissive member 16 is then secured to the coupling mechanism 20 such that the energy transmissive member is fixedly positioned with respect to the optical fiber 13 and the handpiece 12.

Once the system is assembled, the operator can manipulate the handpiece 12 such that the energy transmissive member 16 rests on the surface of the tissue. The operator then actuates the system to apply laser energy to the treatment site 25 in accordance with predetermined exposure criteria. The laser energy is then focused to a location at or below the surface of the treatment site, with or without the aid of the energy transmissive member 16. The distance below the skin surface to which the laser energy is focused can vary from about zero to about five millimeters.

The positional relationship of the energy transmissive member 16 and the surface of tissue, i.e., the epidermal layer, remains substantially constant even as the operator applies pressure to the handpiece. That is, the tissue-contacting surface of the energy transmissive member 16 can impinge upon the tissue surface, but the depth of target tissue below the tissue surface with respect to the tissue-contacting surface remains constant. Thus, handpiece pressure does not alter the depth below the tissue surface to which the laser energy penetrates tissue.

During the course of treating tissue with laser energy, tissue eruptions may occur and tend to splatter the handpiece with tissue debris. Such debris can adhere to and block the distal end of the optical fiber 13, and tend to block or distort laser energy. The energy transmissive member 16 is effective to protect the distal end of the optical fiber 13 and the handpiece 12 from fouling due to such tissue eruptions.

The laser positioning system preferably includes a series of energy transmissive members 16, each having different dimensions and optical characteristics. Each of the energy transmissive members 16 are removably and replaceably mountable to the spacer member 14 and can be disposed of after use.

Prior to conducting a surgical procedure, an operator selects an energy transmissive member 16 that is appropriate for a particular treatment site and/or tissue depth and secures it in the spacer member 14. Alternatively, a spacer member of a suitable length, with a desired pre-attached energy transmissive member is secured to the handpiece 12. The operator then manipulates the handpiece 12 into position and applies laser energy to a treatment site. The selected energy transmissive member 16 protects the distal end of the optical fiber 13 from tissue debris, that may result from the treatment. Optionally, the energy transmissive member 16 is effective to focus the laser energy upon the treatment site.

The components of the laser positioning system are selected from materials suitable for the particular component. For example, the spacer member 14 can be formed from a suitably rigid material including polymers and metals such as stainless steel and aluminum. An exemplary embodiment uses a stainless steel spacer member. The energy transmissive member 16 can be formed from a variety of materials well known to those having ordinary skill in the art, that allow the passage of laser energy. Suitable materials include glass, polymers, sapphire and quartz.

Having described the preferred embodiments of the invention, it will now become apparent to one of ordinary skill in the art that other embodiments incorporating their concepts may be used. Therefore, the invention is not be limited to the particular embodiments disclosed herein, but rather only by the spirit and scope of the appended claims. All publications and references cited herein are expressly incorporated herein by reference in their entirety.

What is claimed is:

1. A positioning system for effecting the delivery of electromagnetic energy to treat tissue, comprising:

a source of electromagnetic energy;

at least one energy delivery handpiece having a proximal end and a distal, energy emitting end;

an optical fiber having a first end in communication with the source of electromagnetic energy and a second end disposed within the handpiece;

at least one elongate spacer member having a first end secured to the handpiece and a second end located a distance from the first end, with a length defined by the distance between the first and second ends of the at least one elongate spacer member; and a plurality of energy transmissive members each having different dimensions and optical characteristics and each being individually removably and replaceably coupled to the second end of the at least one spacer member, wherein the energy transmissive members are effective to shield the handpiece from tissue projected from the treatment area.

2. The system according to claim 1, wherein the at least one elongate spacer member is removably and replaceably secured to the handpiece.

3. The system according to claim 1, wherein the energy transmissive members are effective to focus laser energy from the laser handpiece to a treatment site.

* * * * *